United States Patent [19]

Roser

[11] Patent Number: 5,149,653
[45] Date of Patent: Sep. 22, 1992

[54] PRESERVATION OF VIRUSES

[75] Inventor: Bruce J. Roser, Balsham, Great Britain

[73] Assignee: Quadrant Bioresources Limited, Cambridge, Great Britain

[21] Appl. No.: 411,473

[22] PCT Filed: Jan. 18, 1989

[86] PCT No.: PCT/GB89/00047
§ 371 Date: Nov. 20, 1989
§ 102(e) Date: Nov. 20, 1989

[87] PCT Pub. No.: WO89/06542
PCT Pub. Date: Jul. 27, 1989

[30] Foreign Application Priority Data

Jan. 21, 1989 [GB] United Kingdom ................ 8801338

[51] Int. Cl.$^5$ .................... C12N 7/00; C12N 1/04; C12N 1/00
[52] U.S. Cl. ................... 435/260; 435/235; 435/948
[58] Field of Search .............. 435/260, 235, 948

[56] References Cited

U.S. PATENT DOCUMENTS

| | | | |
|---|---|---|---|
| 3,674,864 | 7/1972 | Angelucci | 435/239 |
| 4,380,582 | 4/1983 | Orlando et al. | 435/260 |
| 4,891,319 | 1/1990 | Roser | 435/188 |
| 5,026,566 | 6/1991 | Roser | 426/443 |

FOREIGN PATENT DOCUMENTS

| | | |
|---|---|---|
| 0192320 | 8/1986 | European Pat. Off. |
| 0230265 | 7/1987 | European Pat. Off. |
| 8705300 | 9/1987 | World Int. Prop. O. |

Primary Examiner—Douglas W. Robinson
Assistant Examiner—Timothy J. Reardon
Attorney, Agent, or Firm—Gottlieb, Rackman & Reisman

[57] ABSTRACT

A method of preserving live viruses comprises subjecting an aqueous system containing the virus to drying either in the frozen state or at ambient temperature, in the presence of trehalose.

3 Claims, No Drawings

PRESERVATION OF VIRUSES

This invention relates to the preservation of live viruses and in particular to the drying of live viruses in a stable form from which they can be reconstituted while retaining their immunogenic or other useful activity.

Live viruses have a number of important uses. The most important is the use of viruses, either intact or attenuated, as immunogenic vaccines. Two good examples are polio virus and measles virus. However, live virus vaccines are extremely difficult to maintain under storage. They cannot, at the moment, be dried and reconstituted without losing their immunogenic effect. Similarly, they cannot be frozen, for the same reason. Consequently, virus vaccines are required to be kept in aqueous media under cool sterile conditions, for example in refrigerators. One of the diseases mentioned above, measles, is of great epidemiological importance, especially in the third world. Each year in Africa alone millions of children die of measles. This is largely because the vaccines necessary for prevention cannot be distributed in the majority of countries concerned which do not have the infrastructure or wealth to provide point-of-use refrigeration.

There is thus a desperate need worldwide for a simple means of preserving viruses in an intact immunogenic form which can be kept without refrigeration or other elaborate control, and which can be reconstituted simply with water just before use.

Other viruses have considerable importance in other fields. For example, Epstein Barr virus (EBV) is of considerable importance in the preparation of human B-cell lines to produce monoclonal antibodies and for studies on human molecular genetics. EBV at present has to be stored in aqueous media under refrigeration.

Similarly, bacteriophages such as phage Lambda derived from E. coli, are of importance in manipulation of DNA and the production of gene libraries in the so-called genetic engineering. Again, this virus must be kept under aqueous conditions under refrigeration.

While it is well-known that drying of unstable biological products, either at room temperature or in the frozen state (lyophilisation) can be aided by adding stabilizing gents to the product in question, there has been no report to our knowledge of the successful stabilization of live viruses.

Thus, for example, UK patent application 2009198A describes the stabilization of meningococcal polysaccharides under lyophilisation, by combining them with various sugars including sucrose, raffinose, glucose and trehalose. In this case, of course, the antigenic component is not a live virus. Similarly. UK Patent application 2126588A describes the stabilization of Tumor Necrosis Factor in the presence of certain sugars and sugar acids.

In European Patent application 140489A1, rubella virus antigen is stabilized by immersion in certain sugars. Again, however, no possibility of stabilizing the virus itself is mentioned.

Our own earlier British patent application 2187191A (WO87/00196) and the corresponding U.S. Pat. No. 4,891,319 describes and claims the preservation of various proteins and other macromolecules at ambient temperature, by drying in the presence of trehalose. Dead virus vaccines are mentioned, but there is no indication that the immunogenic and other functions of live viruses can be preserved in this way.

We have now found that the presence of trehalose in the viral medium during drying either frozen or at ambient temperature, enables live viruses to be preserved and subsequently reconstituted while retaining substantially all their immunogenic properties or other useful properties, including viability. Thus, for the first time, the possibility is provided of having stable dry formulations of vaccines such as polio and influenza viruses.

According to the present invention there is provided a method of preserving live viruses comprising subjecting an aqueous system containing the virus to drying either in the frozen state or at ambient temperature, in the presence of trehalose.

In general, the more trehalose added the better, although in practice beneficial effects are obtained if the aqueous system contains from 1 to 20% by weight of trehalose, typically 5 to 10% by weight. Naturally, the amount of trehalose added will, in part, depend on the amount of virus present in the system, but the exact ratio of trehalose to virus is not particularly critical.

While the virus system can then be lyophilized successfully using standard techniques, to provide a dry material which can be stored at ambient temperatures for subsequent reconstitution with water, it is in fact possible to dry the aqueous system at ambient temperatures without loss of immunogenic or other activity. Thus, for example, an aqueous preparation containing bacteriophage lambda GT10 and 10% by weight trehalose was dried at room temperature (about 20° C.) and was subsequently reconstituted by addition of an aqueous suspension of E. coli in an aqueous medium.

The following examples illustrate the invention further

EXAMPLE 1

Evaluation of the Effect of Trehalose on the Preservation of Epstein Barr Virus at Room Temperature in the Dry State Materials and Methods.

1. Virus production,

The B95.8 producer cell line (The Epstein Barr Virus, Ed. Epstein and Achong, Springer Verlag, Berlin 1979) was grown to confluence in DMEM/10% FCS, 30 ng/ml of 12-O-tetradeconyl-phorbol-13-acetate (TPA) was added, and the culture was mainted at 33° C. for 10 days. The supernatant was collected, clarified through a 0.45 $\mu$m filter and concentrated by ultrafiltration (300 Kdalton nominal cut off) of 40× relative to the original culture.

2. Drying and Storage

To aliquots of the concentrated virus equal volumes of preservative (2%, 20% or 40% trehalose (Sigma) in water) was added, and half of each solution was stored at 4° C. The other half was freeze dried in a glass ampoule and stored at room temperature. After 1 week the freeze dried material was reconstituted with sterile water and dilutions were prepared from each sample using DMDM/10% FCS to yield final virus dilution (relative to the original culture supernatant) of $\frac{1}{8}$.

3. $^3$H Thymidine Incorporation Proliferation Assay.

To each final virus dilution human tonsillar B cells were added to $10^6$/ml and incubated for 90 minutes with gentle agitation to effect viral infection. The cells were then collected by centrifugation, resuspended at $5 \times 10^5$/ml and 0.2 ml aliquots ($10^5$ cells) plated/well of a 96-well flat tissue culture plate, three wells being plated for each condition. After 5 days incubation at 37°

C. 1 μCi of $^3$H Thymidine was added per well and after a 6 hour incubation the wells were harvested and incorporated $^3$H Thymidine counted on a Beta counter.

| Sample | Results. Cpm | % |
|---|---|---|
| EBV at 4° C. | 64528 ± 9702 | (100) |
| EBV freeze dried | 5641 ± 560 | 9 |
| EBV + 1% trehalose | 11860 ± 1466 | 18 |
| EBV + 10% trehalose | 37757 ± 5663 | 58.5 |
| EBV + 20% trehalose | 41793 | 65 |

Additionally, electron microscopy of negatively stained preparations showed that in the presence of 10% trehalose the ultrastructure of dried EBV was preserved, while in the absence of trehalose the ultrastructure is completely disrupted.

EXAMPLE 2

E. Coli bacteriophage (Lambda) GT10

Background

Bacteriophage lambda is capable of infecting E. Coli and entering either the lytic or the lysogenic pathway. In the lytic pathway the phage relicates in the host and eventually lyses the host, releasing all the phage. In the lysogenic pathway instead of replicating and lysing the bacterial hosts the phage DNA enters the hosts genome and replicates with it. The gene responsible for controlling entry into lysogenic or lytic pathways is the phage repressor gene (C1). Phage λ carrying an insert, is seeded onto agar plates, the bacterial lawn contains clear areas (plaques) which are the sites of bacterial cell lysis due to phage replication and proliferation.

Experiment 1:

A single plaque was removed from an agar plate and stored in 1 ml of SM buffer 5.8 gm NaCl, 2 gm MgSO$_4$.7H$_2$O, 5 ml of 1M Tris/HCl pH 7.5 and 5 ml 2% gelatin made up to 1 liter) at 4° C.

A 1 in 1000 dilution was made from this stock in SM buffer. Aliquots of either 1 μl or 10 μl were taken and placed in polypropylene Eppendorf tubes with an equal volume of 20% trehalose in distilled water. Samples were dried at room temperature. The smaller volumes were dried in a laminar flow hood overnight and the larger volumes were dried in a dessicator attached to an evacuating air line. The samples were maintained in a dry state for 24-48 hours. For the plaque assay, 100 μl of a suspension of E. Coli (approximately 8×10$^7$ of strain NM 514) in 10 mM MgSO$_4$ was added to each dried phage sample and incubated at 37° C. for 30 minutes. After incubation, 10 mls of λ top agar (1% Bactotryptone, 0.5% Bacto-yeast extract, 0.5% NaCl, 0.25% MgSO$_4$ and 1% (Bacto-agar) at 42° C. was added to each sample plated out onto previously prepared L-Agar plates. These were left to cool, inverted and incubated at 37° C. for approximately 16 hours, after which the number of plaques was counted.

| Treatment of phage | Results: Dilution of stock | Number of plaques/plate |
|---|---|---|
| Storage at 4° C. in SM buffer | 1 μl of 1/1000 dilution | 47 |
| Dried in SM buffer | 1 μl of 1/1000 dilution | 0 |
| Dried in 10% trehalose | 1 μl of 1/1000 dilution | 19 (40% plaquing efficiency |

| Treatment of phage | Results: Dilution of stock | Number of plaques/plate of control) |
|---|---|---|

Experiment 2

Long-Term Storage

The previous experiment gave details of how bacteriophage lambda carrying an insert can be dried in trehalose, with the preservation of function on rehydration. The bacteriophages in these experiments were rehydrated 24 to 48 hours after drying and were shown to be capable of adsorbing and then penetrating an E. coli host bacterium and then replicating, maturing and finally lysing the host to release many new bacteriophages.

The following experiment tests the ability of trehalose to preserve bacteriophage lambda, so it can be rehydrated and still function, for longer periods and under adverse conditions. A 10% overal aliquot was taken from a stock of bacteriophage lambda, and placed in an Eppendorf tube along with an equal volume of 20% glucose or SM buffer or 20% trehalose or Luria Broth. The stock of bacteriophage lambda used was made by placing a single plaque from an agar plate culture in 1 ml of SM buffer. The samples were dried down in a desiccator attached to an evacuating air line, for at least 16 hours, and then the tops were screwed on the Eppendorfs. Until they were rehydrated the Eppendorfs containing the samples were kept under a variety of conditions. They were placed on the bench at normal room temperature which varied depending on the time of day and the seasons. They were kept in the dark or in direct sunlight. They were placed at 4° C. After 10 months they were rehydrated in a 100 μl suspension of E. coli (approximately 8×10$^7$) in 10 mM MgSO$_4$ and incubated following thorough mixing at 37° C. for about 30 minutes. After incubation 4 mls of lambda top agar at 42° C. was added to each sample and plated out onto previously prepared L-agar plates. These were left to cool and then incubated at 37° C. for approximately 16 hours. The number of plaques was counted.

| Phage dried in following | Number of Plaques/Plate |
|---|---|
| 10% Glucose | Nil |
| 5M Buffer | Nil |
| Luria Broth | Nil |
| 10% Trehalose | 118 |

This gives a value of 12×10$^6$ plaque forming units per ml of stock. This compares with 47×10$^6$ pfu obtained in the assay carried out 10 months previously of the same stock and with 19×10$^6$ pfu in samples rehydrated immediately after desiccation in trehalose buffer.

EXAMPLE 3

Poliovirus Type 3

50 μl virus stock +50 μl 20% trehalose were dried at 37° C. and stored at this temperature for either 24 hours or 7 days before rehydration and assay as compared with virus dried without trehalose and non-dried virus.

Figures shown are the drop in cytopathic titre in logs (base 10).

|  | 24 Hr | 7 D |
| --- | --- | --- |
| With trehalose | 3.4 | 3.7 |
| Without trehalose | 5.9 | 6.0 |
| Non-dried | 0.5 | 0.8 |

Thus, trehalose shows a marked protective effect especially on storage at 37° C.

EXAMPLE 4

Influenza Virus strain X79 (A/phil/2/82 x pR/8 H3N2) ER340

50 µl virus +50 µl 20% trehalose were dried at room temperature and stored at this temperature for 48 hours then reconstituted with Dulbecco's MEM tissue culture medium, 10 µl samples transferred to MDCK cells (FB24) and incubated for 48 hours. The haemagglutination titre was then checked.

|  | Titre |
| --- | --- |
| With trehalose | 7.0 |
| Without trehalose | 4.5 |
| Non-dried | 7.0 |

Thus, trehalose protects completely at this temperature. Other regimes of drying and storage with both polio and flu showed much less or no protection.

The liquid MEV was lyophilised with and without 10% added trehalose and shipped to United Vaccines in Madison Wis. who reconstituted the preparations with normal saline mixed in the dried components and assayed the vaccines for their ability to protect immunised mink against lethal challenge with live Mink Enteritis Virus

|  | Live/Challenged |
| --- | --- |
| With trehalose | 5/5 |
| Without trehalose | 1/5 | i.e. the immunogenicity of this very desiccation-sensitive virus is preserved by trehalose.

I claim:

1. A method of preserving an infectious virion for subsequent reconstitution, the method comprising subjecting an aqueous system containing the infectious virion and trehalose to drying either in the frozen state or at ambient temperature so as to produce a preserved infectious virion, whereby upon rehydration said preserved infectious virion is a reconstituted infectious virion.

2. A method according to claim 1 in which the aqueous system contains 1 to 20% by weight of trehalose.

3. A method according to claim 1 in which the aqueous system contains 5 to 20% by weight of trehalose.

* * * * *